Figure 1:
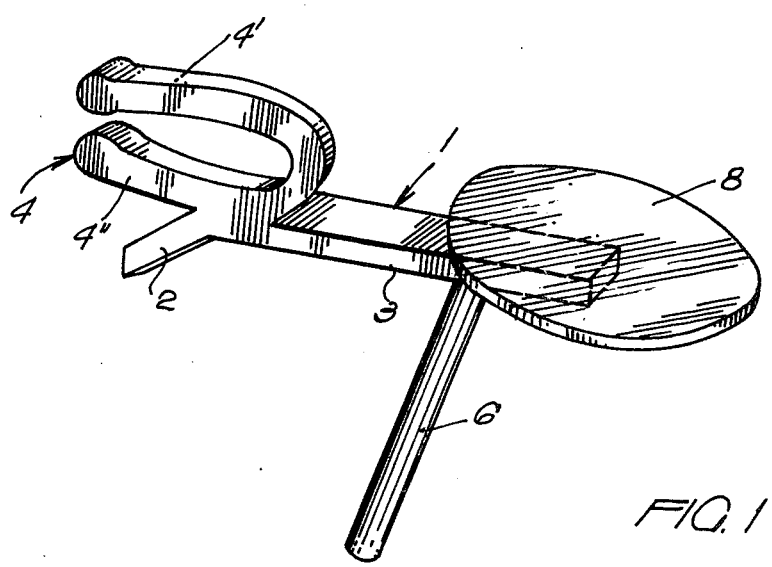

United States Patent [19]

Mercandino

[11] 4,130,905
[45] Dec. 26, 1978

[54] ARTIFICIAL MALLEUS COLUMELLA FOR THE HUMAN EAR

[76] Inventor: Eduardo C. C. Mercandino, Montevideo 606, Buenos Aires, Argentina

[21] Appl. No.: 803,335

[22] Filed: Jun. 3, 1977

[51] Int. Cl.$^2$ .............................................. A61F 1/24
[52] U.S. Cl. ............................................... 3/1.9
[58] Field of Search .................... 3/1, 1.9; 128/350 R, 128/350 V

[56] References Cited

U.S. PATENT DOCUMENTS

| 3,473,170 | 10/1969 | Haase et al. | 3/1 |
| 3,823,423 | 7/1974 | Mercandino | 3/1 |

Primary Examiner—Ronald L. Frinks
Attorney, Agent, or Firm—Ladas, Parry, Von Gehr, Goldsmith & Deschamps

[57] ABSTRACT

This invention provides an improvement in an artificial malleus columella for the human ear of the type comprising an elongated laminar part conformed in an obtuse angle. Resilient fixing means projects from the laminar part to permit attachment to the bridge of the human ear and a stem is fixed by one end to a face of said laminar part. The other end of the stem contacts the stapes. The resilient fixing means projects away from the mentioned angle and is in the form of a clamp. A disc like element is arranged on the laminar part at a location remote from said clamp.

4 Claims, 2 Drawing Figures

ARTIFICIAL MALLEUS COLUMELLA FOR THE HUMAN EAR

The invention relates to an improvement in an artificial malleus columella to be placed in the human ear in cases of necrosis or absence of the natural columella, originated by chronic suppuration of the ear.

U.S. Pat. No. 3,823,423 to Mercandino teaches the mounting of an artificial malleus columella on the bridge after appropriate drilling by a surgeon. The mounting of such an artificial malleus columella permits audio recovery of the patient at least to such a degree as to allow him to work and live normally. The artificial malleus columella of Mercandino Patent 3,823,423 is simple to make as it comprises a laminar plastic material part obtusely angled with the base of the angle having a fixation device to fix it to said bridge. In addition, a stem is provided to contact the footplate of the stapes or the head of the stapes, thus re-establishing the required continuity between the ear drum and the stapes, to restore hearing.

The invention has now found that if fixing means in the form of a clamp is placed in the face externally of the obtuse angle and on one of the branches of the clamp, then the device can be placed under the bridge at the level of the Sulcus Timpanicus. In addition, the sound transmission can be improved by the incorporation of a disc like element which enlarges the contact surface with the ear drum.

Such location is advantageous for a number of reasons. In particular, it enables the disc mounted on the branch remote from the clamp to be located below the level of the bridge, thereby diminishing the possibility of perforation of the ear drum.

In addition, the mounting of the device under the bridge permits placing the device nearer to the stapes and therefore using a shorter stem.

This invention can be put into practice in the size, colors, materials and shapes that may be found to be more convenient for the purposes of the device.

Figure 2:
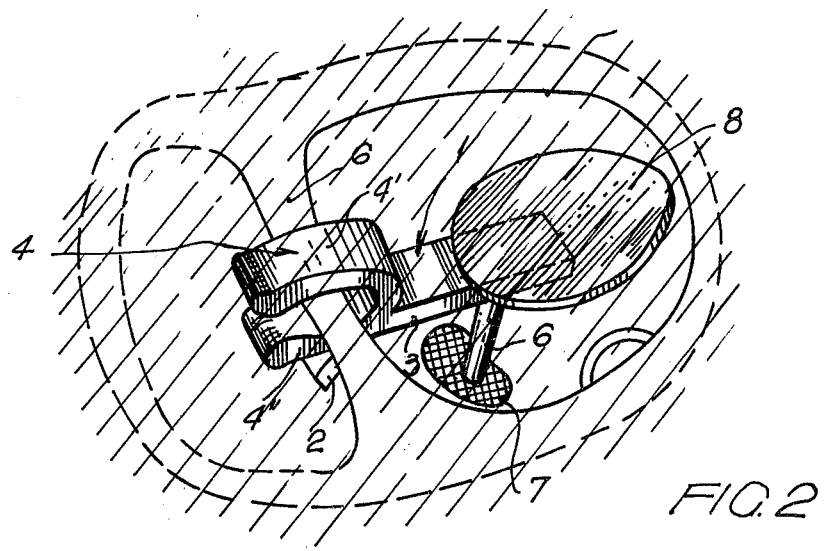

In order that the invention may be clearly understood and put into practice, it will hereinafter be described in detail with reference to the accompanying drawing, in which:

FIG. 1 illustrates in perspective an improved artificial malleus columella of the invention, and FIG. 2 illustrates the embodiment of FIG. 1, placed and retained in position.

With reference to the drawing, the improvement is made in an artificial malleus columella of the type comprising a preferably integral part 1 made of plastics material and having an obtuse angle laminar shape defining two approximately rectangular laminar planes or linear portions 2 and 3 of different lengths.

On the external side of said angle, the improved device is provided with fixing means in the form of a clamp 4 with resilient branches 4' and 4". These branches are conveniently curved and directed towards the end portion of the laminar plane of shoter length 2. The median plane of the clamp 4 is substantially perpendicular to the shorter laminar plane 2 and, in this manner, the prosthesis can be mounted over the bridge 5 as shown in FIG. 2.

A disc 8 is located above and at the end of the longer laminar plane 3 and is partially or totally malleable, and a stem 6 depends from the underside of said longer plane 3 to rest on the stapes 7 of the middle ear.

The improvement afforded by this invention allows the surgeon to mount the prosthesis under the bridge 5 at the level of the Sulcus Timpanicus.

It is understood that this invention is not limited in any way by the described and illustrated embodiment, but different modifications may be encompassed within the scope of the claims.

I claim:

1. An artificial malleus columella for the human ear comprising an elongated member angled downwardly at a point along its length to provide first and second linear portions, said angle being an obtuse angle, a stem depending from the underside of the first linear portion to contact the stapes of the middle ear when the artificial malleus columella is in position and a clamp adapted to engage the bridge of the ear and being located on the external surface of the obtuse angle and extending over the second linear portion whereby the artificial malleus columella will be held in position below the level of said bridge.

2. An artificial malleus columella according to claim 1, wherein the clamp is substantially C-shaped with the limbs of the clamp extending substantially parallel to said first linear portion and directed outwardly.

3. An artificial malleus columella according to claim 2, wherein a disc shaped element is mounted on the upper surface of the first linear portion at the end remote from said C-shaped clamp.

4. An artificial malleus columella according to claim 1, wherein said artificial malleus columella is of plastics material.